（12） United States Patent
Steiner et al.

(10) Patent No.: US 7,713,929 B2
(45) Date of Patent: May 11, 2010

(54) RAPID ACTING AND LONG ACTING INSULIN COMBINATION FORMULATIONS

(75) Inventors: Solomon S. Steiner, Mount Kisco, NY (US); Roderike Pohl, Sherman, CT (US)

(73) Assignee: Biodel Inc., Danbury, CT (US)

( * ) Notice: Subject to any disclaimer, the term of this patent is extended or adjusted under 35 U.S.C. 154(b) by 67 days.

(21) Appl. No.: 11/695,562

(22) Filed: Apr. 2, 2007

(65) Prior Publication Data

US 2008/0039365 A1 Feb. 14, 2008

Related U.S. Application Data

(60) Provisional application No. 60/744,687, filed on Apr. 12, 2006.

(51) Int. Cl.
*A61K 38/28* (2006.01)
*A61K 38/16* (2006.01)
*A61K 31/185* (2006.01)
*C07K 14/62* (2006.01)

(52) U.S. Cl. ............... 514/3; 514/2; 514/12; 530/300; 530/303; 530/324

(58) Field of Classification Search .................. None
See application file for complete search history.

(56) References Cited

U.S. PATENT DOCUMENTS

| | | |
|---|---|---|
| 2,143,590 A | 1/1939 | Scott |
| 2,626,228 A | 1/1953 | Petersen |
| 2,819,999 A | 1/1958 | Schlichtkrull |
| 3,649,456 A | 3/1972 | De Benneville et al. |
| 3,683,635 A | 8/1972 | Campanelli |
| 3,906,950 A | 9/1975 | Cocozza |
| 3,921,637 A | 11/1975 | Bennie et al. |
| 4,129,560 A | 12/1978 | Zoltobrocki |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,343,898 A | 8/1982 | Markussen |
| 4,377,482 A | 3/1983 | Rivier |
| 4,459,226 A | 7/1984 | Grimes |
| 4,489,159 A | 12/1984 | Markussen |
| 4,511,505 A | 4/1985 | Morihara |
| 4,659,696 A | 4/1987 | Hirai et al. |
| 4,861,627 A | 8/1989 | Mathiowitz |
| 4,866,051 A | 9/1989 | Hunt |
| 4,946,828 A | 8/1990 | Markussen |
| 5,006,343 A | 4/1991 | Benson |
| 5,042,975 A | 8/1991 | Chien |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,352,461 A | 10/1994 | Feldstein et al. |
| 5,354,562 A | 10/1994 | Platz |
| 5,364,838 A | 11/1994 | Rubsamen |
| 5,458,135 A | 10/1995 | Patton et al. |
| 5,474,978 A | 12/1995 | Bakaysa |
| 5,482,927 A | 1/1996 | Maniar |
| 5,484,606 A | 1/1996 | Dhabhar et al. |
| 5,492,112 A | 2/1996 | Mecikalski et al. |
| 5,503,852 A | 4/1996 | Steiner et al. |
| 5,514,646 A | 5/1996 | Chance et al. |
| 5,534,488 A | 7/1996 | Hoffmann |
| 5,547,929 A | 8/1996 | Anderson, Jr. et al. |
| 5,562,909 A | 10/1996 | Allcock et al. |
| 5,577,497 A | 11/1996 | Mecikalski et al. |
| 5,650,486 A | 7/1997 | Felippis |
| 5,653,961 A | 8/1997 | McNally et al. |
| 5,653,987 A | 8/1997 | Modi et al. |
| 5,658,878 A | 8/1997 | Bäckström et al. |

(Continued)

FOREIGN PATENT DOCUMENTS

CA 2 136 704 5/1995

(Continued)

OTHER PUBLICATIONS

FDA Approves Rapid-Acting Insulin Apidra® from Treatment of Children With Diabetes from http://www.medicalnewstoday.com/articles/127409.php, pp. 1-6. Accessed Apr. 30, 2009.*

(Continued)

*Primary Examiner*—Anish Gupta
*Assistant Examiner*—Julie Ha
(74) *Attorney, Agent, or Firm*—Pabst Patent Group LLP

(57) ABSTRACT

A combined rapid acting-long acting insulin formulation has been developed in which the pH of the rapid acting insulin is decreased so that the long acting glargine remains soluble when they are mixed together. In the preferred embodiment, this injectable basal bolus insulin is administered before breakfast, provides adequate bolus insulin levels to cover the meal, does not produce hypoglycemia after the meal and provides adequate basal insulin for 24 hours. Lunch and dinner can be covered by two bolus injections of a fast acting, or a rapid acting or a very rapid acting insulin. As a result, a patient using intensive insulin therapy should only inject three, rather than four, times a day.

14 Claims, 4 Drawing Sheets

U.S. PATENT DOCUMENTS

| | | | |
|---|---|---|---|
| 5,672,359 A | 9/1997 | Digenis |
| 5,693,338 A | 12/1997 | Milstein |
| 5,740,794 A | 4/1998 | Smith et al. |
| 5,747,445 A | 5/1998 | Bäckström et al. |
| 5,763,396 A | 6/1998 | Weiner et al. |
| RE35,862 E | 7/1998 | Steiner et al. |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,898,028 A | 4/1999 | Jensen |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,132,766 A | 10/2000 | Sankaram et al. |
| 6,153,613 A | 11/2000 | Ono et al. |
| RE37,053 E | 2/2001 | Hanes et al. |
| 6,248,363 B1 | 6/2001 | Patel et al. |
| 6,254,854 B1 | 7/2001 | Edwards et al. |
| 6,264,981 B1 | 7/2001 | Zhang |
| 6,294,204 B1 | 9/2001 | Rossling et al. |
| 6,310,038 B1 | 10/2001 | Havelund |
| 6,331,318 B1 | 12/2001 | Milstein |
| 6,395,744 B1 | 5/2002 | Adams et al. |
| 6,395,774 B1 | 5/2002 | Milstein |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,444,226 B1 | 9/2002 | Steiner et al. |
| 6,447,753 B2 | 9/2002 | Edwards et al. |
| 6,465,425 B1 | 10/2002 | Tracy |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger |
| 6,685,967 B1 | 2/2004 | Patton |
| 6,737,045 B2 | 5/2004 | Patton |
| 6,949,258 B2 | 9/2005 | Zhang |
| 6,960,561 B2 | 11/2005 | Boderke |
| 7,030,084 B2 | 4/2006 | Ekwuribe et al. |
| 7,089,934 B2 | 8/2006 | Staniforth et al. |
| 7,192,919 B2 | 3/2007 | Tzannis et al. |
| 7,279,457 B2 | 10/2007 | Pohl et al. |
| 2001/0039260 A1 | 11/2001 | Havelund |
| 2001/0043934 A1 | 11/2001 | L'Italien et al. |
| 2002/0198140 A1 | 12/2002 | Havelund |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0172924 A1 | 9/2003 | Staniforth et al. |
| 2003/0194420 A1 | 10/2003 | Holl et al. |
| 2004/0077528 A1 | 4/2004 | Steiner |
| 2004/0096403 A1 | 5/2004 | Steiner |
| 2004/0151774 A1 | 8/2004 | Pauletti et al. |
| 2004/0157928 A1 | 8/2004 | Kim et al. |
| 2004/0182387 A1 | 9/2004 | Steiner |
| 2004/0247628 A1 | 12/2004 | Lintz et al. |
| 2005/0080000 A1 | 4/2005 | Thurow et al. |
| 2005/0153874 A1 | 7/2005 | Cheatham |
| 2005/0203001 A1 | 9/2005 | Arbit et al. |
| 2005/0214251 A1 | 9/2005 | Pohl et al. |
| 2006/0067891 A1 | 3/2006 | Modi |
| 2007/0086952 A1 | 4/2007 | Steiner et al. |
| 2007/0134279 A1 | 6/2007 | Stern |
| 2007/0155654 A1 | 7/2007 | Langkjaer |
| 2007/0235365 A1 | 10/2007 | Pohl et al. |
| 2008/0039368 A1 | 2/2008 | Steriner et al. |
| 2008/0085298 A1 | 4/2008 | Pohl et al. |
| 2008/0090753 A1 | 4/2008 | Pohl et al. |
| 2008/0096800 A1 | 4/2008 | Pohl et al. |

FOREIGN PATENT DOCUMENTS

| | | |
|---|---|---|
| DE | 247684 | 7/1987 |
| EP | 0/069/715 | 1/1983 |
| EP | 0/122/036 | 10/1984 |
| EP | 0 220 958 A2 | 5/1987 |
| EP | 0/237/507 | 9/1987 |
| EP | 0 257 915 | 2/1988 |
| EP | 0/360/340 | 3/1990 |
| EP | 0/364/235 | 4/1990 |
| EP | 0/606/486 | 12/1993 |
| EP | 0748213 | 12/1996 |
| EP | 1/114/644 | 7/2001 |
| EP | 1 428 524 | 6/2004 |
| EP | 96911738 | 6/2004 |
| GB | 2 069 502 | 8/1981 |
| GB | 2240337 | 7/1991 |
| JP | 0149545 | 2/1992 |
| JP | 363020301 A | 1/1998 |
| WO | 0 220 958 A2 | 5/1987 |
| WO | WO 90/13285 | 11/1990 |
| WO | WO 91/04011 | 4/1991 |
| WO | WO 91/08764 | 6/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | WO 93/17728 | 9/1993 |
| WO | WO 93/18754 | 9/1993 |
| WO | WO 94/00291 | 1/1994 |
| WO | WO 95/00127 | 1/1995 |
| WO | WO 95/11666 | 5/1995 |
| WO | WO 95/31979 | 11/1995 |
| WO | WO 95/34294 | 12/1995 |
| WO | WO 96/10996 | 4/1996 |
| WO | WO 96/36314 | 11/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 99/52506 | 10/1999 |
| WO | WO 01/00654 | 1/2001 |
| WO | WO 01/07107 | 2/2001 |
| WO | WO 02/11676 | 2/2002 |
| WO | WO 03/057170 | 7/2003 |
| WO | WO 03/086345 | 10/2003 |
| WO | WO 03/094951 | 11/2003 |
| WO | WO 03/101395 | 12/2003 |
| WO | WO 2004/056314 | 7/2004 |
| WO | WO 2004/075919 | 9/2004 |
| WO | WO 2004/080401 | 9/2004 |
| WO | WO 2005/089722 | 9/2005 |
| WO | WO 2006/088473 | 8/2006 |
| WO | WO 2007/041481 | 4/2007 |
| WO | WO 2007/047948 | 4/2007 |

WO WO 2007/121256 10/2007

OTHER PUBLICATIONS

Lantus Prescrigin Information-Aventis Pharmaceuticals from http://products.sanofi-aventis.us/lantus/lantus.html, pp. 1-45. Accessed Apr. 30, 2009.*
Levemir from www.levemir.com, pp. 1-15. Accessed Apr. 30, 2009.*
Insulin from Diabetes Forecast, 2008 Resource Guide, RG11-RG14. 2008.*
Edelman, et al., "A double-blinded placebo-controlled trial assessing pramlintide treatment in the setting of intensive insulin therapy in type 1 diabetes", Diabetes Care, 29(10:2189-2195 (2006).
Nilsson, et al., "Low levels of asparagine deamidation can have a dramatic effect on aggregation of amyloidogenic peptides: implications for the study of amyloid formation", Protein Science, 11(2): 342-349 (2002).
U.S. Appl. No. 12/324,717, filed Nov. 28, 2008, Steiner, et al.
"Human Insulin", GenBank Accession No. AAA59172, pp. 1-2, accessed Feb. 17, 2009.
"Bovine Insulin", GenBank Accession No. ACD35246, pp. 1-2, accessed Feb. 17, 2009.
"Types of Insulin", http://www.diabetes.org/for-parents-and-kids/diabetes-care/types-actions.jsp, pp. 1-2, accessed Feb. 17, 2009.
Davidson, et al., "Effect of premixed nph and regular insulin on glucose control and health-related quality of life in patients with type 2 diabetes mellitus", Endocrine Practice, 3(6):331-336 (1997).
Aungst & Rogers, "Site dependence of absorption-promoting actions of laureth-9, Na salicylate, Na2EDTA, and aprotinin on rectal, nasal, and buccal insulin delivery", Pharm. Res., 5(5):305-308 (1988).
Brange, et al., Chemical stability of insulin 1: hydrolytic degradation during storage of pharmaceutical preparations, Pharm. Res., 9:715-726 (1992).
De Sousa, et al., "Biocompatibility of EDTA, EGTA and citric acid", Braz. Dent. J., 16:3-8 (2005).
Kang, et al., "Subcutaneous insulin absorption explained by insulin's physiochemical properties", Diabetes Care, 14:942-948 (1991).
Keowmaneechai, et al., "Influence of EDTA and citrate on physiochemical properties of whey protein-stabilized oil-in-water emulsions containing $CaCl_2$", J. Agricultural and Food, Chemistry, 50:7145-7153 (2002).
Klauser, et al., "Mixtures of human intermediate and human regular insulin in type 1 diabetic patients", Diabetes Res. and Clin. Practice, 5:185-190 (1988).
Monch & Dehnen, "High-performance liquid chromatography of polypeptides and proteins on a reversed-phase support", Journal of Chromatography, 147:415-418 (1978).
Quinn, et al., "Minimizing the aggregation of insulin solutions", J. Pharmaceutical Sci., 72:1472-1473 (1983).
Szepesy & Horvath, "Specific salt effects in hydrophobic interaction chromatography of proteins", Chromatographia, 26:13-18 (1988).
Todo, et al., "Effect of additives on insulin absorption from intracheally administered dry powders in rats", Int. J. Pharmaceutics, 220:101-110 (2001).
Bauer, et al., "Assessment of beta-adrenergic receptor blockade after isamoltane, a 5-HT1-receptor active compound, in healthy volunteers," Clin. Pharmacol Ther 53:76-83 (1993).
Benita, "Characterization of Drug-Loaded Poly(d,l-lactide) Microspheres," J. Pharm. Sci.,73: 1721-1724 (1984).
Bensch, et al., "Absorption of intact protein molecules across the pulmonary air-tissue barrier," Science 156: 1204-1206 (1967).
Brange, et al., "Insulin Structure and stability", Pharm Biotechnol., 5:315-50 (1993).
Cerasi, et al., "Decreased sensitivity of the pancreatic beta cells to glucose in prediabetic and diabetic subjects. A glucose dose-response study," Diabetes 21(4): 224-34 (1972).
Cefalu, et al, "Inhaled Human Insulin Treatment in Patients with type 2 diabetes mellitus," Ann. Int. Med., 134: 203-7 (2001).
Cheatham and Pfeutzner, "Desirable dynamics & performance of inhaled insulin compared to subcutaneous insulin given at mealtime in type 2 diabetes: A report from the technosphere/insulin study group" Diabetes Technology & Therapeutics 6:234-235 (2004).

Costello, et al., "Zinc inhibition of mitochondrial aconitase and its importance in citrate metabolism in prostate epithelial cells", Journ. Biol. Chem., 272(46):28875-28881 (1997).
Dieter Köhler, "Aerosols for Systemic Treatment", Lung (Suppl), 677-684 (1990).
Dunn, "Zinc-ligand interactions modulate assembly and stability of the insulin hexamer", Biometals, 18(4):295-303 (2005).
Edelman, "Type II Diabetes Mellitus," Advances in Internal Medicine, 43:449-500 (1998).(Abstract).
Elliott, et al., "Parenteral absorption of insulin from the lung in diabetic children," Austr. Paediatr. J. 23: 293-297 (1987).
Engelgau, et al., "Screening for tyoe 2 diabetes," Diabetes Care 1563(23):1-31 (2000).
Festa, et al., "LDL particle size in relation to insulin, proinsulin, and insulin sensitivity" Diabetes Care 22(10):1688-1693 (1999).
Garber, "Premixed insulin analogues for the treatment of diabetes mellitus", Drugs, 66(1):31-49 (2006).
Gupta, "Contemporary Approaches in Aerosolized Drug Delivery to the Lung," J. Controlled Release, 17(2): 127-147 (1991).
Haffner, et al., "Proinsulin and insulin concentrations I relation to carotid wall thickness" Stroke 29:1498-1503 (1998).
Hagedorn, et al., "Protamine insulin", JAMA, 106:177-180 (1936).
Hanley et al., "Cross-sectional and prospective associations between proinsulin and cardiovascular disease risk factors in a population experiencing rapid cultural transition" Diabetes Care 24(7):1240-1247 (2001).
Heubner, et al. Klinische Wochenschrift 16,2342 (1924).
Heyder, "Alveolar deposition of inhaled particles in humans," Am. Ind. Hyg. Assoc. J. 43(11): 864-866 (1982).
Heyder, "Particle Transport onto Human Airway Surfaces" Eur. J. Respir. Dis. Suppl. 119, 29-50 (1982).
Johnson, et al., "Turbuhaler®: a new device for dry powder terbutaline inhalation," Allergy 43(5):392-395 (1988).
Jones, et al., "An investigation of the pulmonary absorption of insulin in the rat", Third European Congress of Biopharmaceutics and Pharmacokinetics, 1987.
Katchalski, "Synthesis of Lysine Anhydride," J. Amer. Chem. Soc., 68: 879-880 (1946).
Kohler, et al., "Pulmonary Administration . . . ," Abstract 298, Diabetes 33 (Suppl.):75A (1984).
Kohler, "Aerosols for Systemic Treatment", Lung Suppl. 677-683 (1990).
Komada, et al., "Intratracheal delivery of peptide and protein agents: absorption from solution and dry powder by rat lung," J. Pharm. Sci. 83(6): 863-867 (1994).
Kontny, et al. "Issues Surrounding MDI Formulation Development with Non-CFC Propellants," J. Aerosol Med. 4(3), 181-187 (1991).
Kopple, "A Convenient Synthesis of 2,5-Piperazinediones," J. Org. Chem., 33(2): 862-864 (1968).
Leahy, "Beta-cell dysfunction in type II diabetes mellitus," Curr. Opin. Endocrinol. Diabetes 2(4): 300-306 (1995).
Lee, et al., "Development of an Aerosol Dosage Form Containing Insulin," J. Pharm. Sci. 65(4), 67-572 (1976).
Lian, et al., "A self-complementary, self-assembling microsphere system: application for intravenous delivery of the antiepileptic and neuroprotectant compound felbamate," J Pharm Sci 89:867-875 (2000).
Lim, "Microencapsulation of Living Cells and Tissues," J. Pharm. Sci., 70: 351-354 (1981).
Mathiowitz, "Morphology of Polyanhydride Microsphere Delivery Systems," Scanning Microscopy, 4: 329-340 (1990).
Mathiowitz, "Novel Microcapsules for Delivery Systems," Reactive Polymers, 6: 275-283 (1987).
Mathiowitz, "Polyanhydride Microspheres As Drug Carriers I. Hot-Melt Microencapsulation," J. Controlled Release, 5: 13-22 (1987).
Mathiowitz, "Polyanhydride Microspheres As Drug Carriers II. Microencapsulation by Solvent Removal," J. Applied Poly. Sci., 35: 755-774 (1988).
Mathiowitz, "Polyanhydride Microspheres IV.Morphology and Characterization of Systems Made by Spray Drying," J. Applied Poly. Sci., 45: 125-134 (1992).
Nagai, et al., "Powder Dosage Form of Insulin for Nasal Administration," J. Control Rel., 1:15-22 (1984).

Okumura, et al., "Intratracheal delivery of insulin. Absorption from solution and aerosol by rat lung," *Int. J. Pharmaceuticals* 88: 63-73 (1992).

Patton & Platz, "Routes of Delivery: Case Studies. Pulmonary delivery of peptides and proteins for systemic action," *Adv. Drug. Del. Rev.* 8: 179-196 (1992).

Pfeiffer, "Insulin secretion in diabetes mellitus," *Am. J. Med.* 70(3): 579-88 (1981).

Pfutzner, et al., "Influence of small dose i.v., s.c. and pulmonary insulin treatment on prandial glucose control in patients with type 2 diabetes" *37th Annual Meeting of the EASD*, Glasgow, Sep. 9-13, 2001 812 (2001) (abstract).

Polonsky, et al., "Abnormal patterns of insulin secretion in non-insulin-dependent diabetes mellitus," *N. England J. Med.* 318(19): 1231-39 (1988).

Prabhu, et al. "A study of factors controlling dissolution kinetic of zinc complexed protein suspensions in various ionic species", *Int. J. Pharm.*, 217(1-2):71-8 (2001).

Raskin, et al., "Continuous subcutaneous insulin infusion and multiple daily injection therapy are equally effective in type 2 diabetes" *Diabetes Care* 26:2598-2603 (2003).

Rosenstock, et al., "Reduced hypoglycemia risk with insulin glargine: a meta-analysis comparing insulin glargine with human NPH insulin in type 2 diabetes", Diabetes Care, 28(4):950-5 (2005).

Sakr, "A new approach for insulin delivery via the pulmonary route: design and pharmacokinetics in non-diabetic rabbits", *International Journal of Pharmaceutics*, 86:1-7 (1992).

Salib, "Utilization of Sodium Alginate in Drug Microencapsulation," *Pharazeutische Industrie*, 40(11a): 1230-1234 (1978).

Sawhney, "Bioerodible Hydrogels Based on Photopolymerized Poly-(ethylene glycol)-co-poly(a-hydroxy acid) Diacrylate Macromers," *Macromolecules*, 26: 581-587 (1993).

Schluter, et al., "Pulmonary Administration of Human Insulin in Volunteers and Type I Diabetics", *Diabetes*, 33 (Suppl.): 298 (1984).

Schneider, et al., "Stimulation by proinsulin of expression of plasminogen activator inhibitor type-I in endothelial cells" *Diabetes* 41(7):890-895 (1992).

Warren, et al., "Postprandial versus preprandial dosing of biphasic insulin aspart in elderly type 2 diabetes patients" *Diabetes Research and Clinical Practive* 66:23-29 (2004).

Waterhouse, et al. "Comparative assessment of a new breath-actuated inhaler in patients with reversible airways obstruction." *Respiration* 59:155-158 (1992).

Wigley, et al., "Insulin across respiratory mucosae by aerosol delivery," *Diabetes* 20(8): 552-556 (1971).

Wigley, et al., "Insulin across respiratory mucosae by aerosol delivery," *Diabetes* 20(8): 552-556 (1971).

Witchert, "Low Molecular Weight PLA: A Suitable Polymer for Pulmonary Administered Microparticles," *J. Microencapsulation*, 10(2): 195-207 (1993).

Yoshida, et al., "Absorption of insulin delivered to rabbit trachea using aerosol dosage form," *J. Pharm. Sci.* 68(5): 670-671 (1979).

Zethelius, et al., "Proinsulin is an Independent Predictor of Coronary Heart Disease" *Circulation* 105:2153-2158 (2002).

U.S. Appl. No. 12/348,839, filed Jan. 5, 2009, Kashyap, et al.

U.S. Appl. No. 12/397,219, filed Mar. 3, 2009, Steiner, et al.

Actrapid, "Summary of product characteristics", http://emc.medicines.org.uk/medicine/3513/SPC/Actrapid+100+IU+ml,+Solution+for+Injection+in+a+vial/, pp. 1-6; revised (2007); (accessed Apr. 20, 2009).

Berge, et al. "Pharmacuetical Salts," *J. Pharmaceutical Sciences* 66(1):1-19 (1997).

Culy, et al., "Management of diabetes mellitus: Defining the role of insulin lispro mix 75/25", *Dis. Man. Health. Outcome*, 9(12): 711-730 (2001).

Heinemann, et al. "Current Status of the development of inhaled insulin" *Br. J. Diabetes Vasc Dis* 4:295-301 (2004).

Humalog®, Mix 75/25TM "Patient Information", Eli Lilly, pp. 1-4, accessed Jun. 18, 2009.

Karl, et al., "Pramlintide as an adjunct to insulin in patients with type 2 diabetes in a clinical practice setting reduced AIC, postprandial glucose excursions, and weight", *Diabetes Technology And Therapeutics*, 9(2):191-199 (2007).

Kashyap, "Design and evaluation of biodegradable, biosensitive in situ gelling system for pulsatile delivery of insulin" *Biomaterials*, 28(11):2051-60 (2007). Epub Jan. 19, 2007.

Koehler, et al. "Non-radioactive approach for measuring lung permeability: inhalation of insulin," *Atemw Lungebkrkh* 13:230-232 (1987).

Lalli, et al., "Long-term intensive treatment of type 1 diabetes with the short-acting insulin analog lispro in variable combination with NPH insulin at mealtime", *Diabetes Care*, 22(3):468-77 (1999).

Molitch, et al., "How long should insulin be used once a vial is started?", *Diabetes Care*, 27(5):1240-1; author reply 1241-2 (2004).

Moren, "Aerosol dosage forms and formulations" in *Aerosols in Medicine*, (2nd ed.), Elsevier, pp. 321-350 (1993).

Plum, et al., "Pharmacokinetics of the rapid-acting insulin analog, insulin aspart, in rats, dogs, and pigs, and pharmacodynamics of insulin aspart in pigs.", *Drug Metab. Dispos.*, 28(2):155-60 (2000).

Raz, et al. "Pharmacodynamic and pharmacokinetics of dose ranging effects of oralin versus s.c. regular insulin in Type 1 diabetic patients," *Fourth Annual Diabetes Technology Meeting*, Philadelphia, PA, 2004.

Roach, et al., "Improved postprandial glycemic control during treatment with Humalog Mix25, a novel protamine-based insulin lispro formulation. Humalog Mix25 Study Group", *Diabetes Care*, 22(8):1258-61 (1999).

Steiner, et al. "Technosphere ™/ Insulin- proof of concept study with new insulin formulation for pulmonary delivery" *Exp. Clin. Endocrinol. Diabetes* 110:17-21 (2002).

Talrose, et al., "Radiation resistivity of frozen insulin solutions and suspensions", *Int. J. Appl. Radiat. Isot.*, 32(10):753-6 (1981).

Traitel, et al., "Characterization of glucose-sensitive insulin release systems in simulated in vivo conditions", *Biomaterials*, 21(16):1679-87 (2000).

Velosulin, "Information for health professionals, Production Data Sheet", http://www.medsafe.gov.nz/profs/datasheet/v/VelosulinMCinj.htm, pp. 1-5; (2000); (accessed Apr. 20, 2009).

Zhang, et al., "Modulated insulin permeation across a glucose-sensitive polymeric composite membrane", *J. Control Release*, 80(1-3):169-78 (2002).

* cited by examiner

RAPID ACTING AND LONG ACTING INSULIN COMBINATION FORMULATIONS

CROSS REFERENCE TO RELATED APPLICATIONS

This application claims priority to U.S. Ser. No. 60/744,687 entitled "Rapid Acting and Long Acting Insulin Combination Formulations" filed Apr. 12, 2006 by Solomon S. Steiner and Roderike Pohl and U.S. Ser. No. 11/537,335 entitled "Rapid Acting and Prolonged Acting Insulin Preparations" filed Sep. 29, 2006 by Solomon B. Steiner and Roderike Pohl.

BACKGROUND OF THE INVENTION

The present invention generally relates to formulations combining rapid acting and long acting insulin formulations.

Intensive insulin therapy for diabetes involves providing a basal insulin, ideally present at a uniform level in the blood over a 24 hour period and a bolus or meal time (prandial) insulin to cover the added carbohydrate load from digestion concomitant with each meal.

In 1936, Hans Christian Hagedorn and B. Norman Jensen discovered that the effects of injected insulin could be prolonged by the addition of protamine obtained from the "milt" or semen of river trout. The insulin was added to the protamine and the solution were brought to pH 7 for injection. In 1946, Nordisk Company was able to form crystals of protamine and insulin and marketed it in 1950 as NPH, (Neutral Protamine Hagedorn, "NPH") insulin. NPH insulin has the advantage that it can be mixed with an insulin that has a faster onset to compliment its longer lasting action. Eventually all animal insulins were replaced by human recombinant insulin.

Until very recently, and in many places today, basal insulin is usually provided by the administration of two daily doses of NPH insulin, separated by 12 hours. A patient eating three meals a day and using NPH insulin as the basal insulin requires five injections per day, one with each of three meals and two NPH insulin injections, one in the morning and the other at bedtime. To reduce the number of injections the patient must take, the morning dose of NPH insulin has been combined with a short acting insulin, (recombinant human insulin) or a rapid acting insulin analog, such as lispro. A typical combination is a 70% NPH to 30% rapid acting insulin analog mixture. As a result, the patient can reduce the number of injections from five per day to four per day. See, for example, Garber, Drugs 66(1):31-49 (2006).

More recently insulin glargine, (tradename LANTUS®) a "very long-acting" insulin analog has become available. It starts to lower blood glucose about one hour after injection and keeps working evenly for 24 hours. J. Rosenstock and colleagues found that patients who took insulin glargine had a much lower risk of low blood glucose (hypoglycemia) than the patients who took NPH insulin.

Glargine cannot be mixed with other short or rapid acting insulins because the mixture causes glargine to precipitate prior to injection and administration of a precipitated insulin makes it virtually impossible to administer a known and reliable dose. The manufacturer of glargine warns users against mixing glargine with any other insulin.

It is therefore an object of the present invention to provide insulin formulations that can be used to reduce the number of daily injections to three.

It is another object of the present invention to provide a basal-bolus insulin formulation.

It is still another object of the present invention to provide a stable insulin formulation having immediate and long term release characteristics.

SUMMARY OF THE INVENTION

A combined rapid acting-long acting insulin formulation has been developed wherein the pH of the rapid acting insulin is decreased through the use of an acid such as aspartic, glutamic or citric acid, so that the long acting glargine remains soluble when they are mixed together. In the most preferred embodiment, a chelator such as EDTA is added to enhance absorption. In the preferred embodiment, this injectable basal bolus insulin is administered before breakfast, provides adequate bolus insulin levels to cover the meal, does not produce hypoglycemia after the meal and provides adequate basal insulin for 24 hours. Lunch and dinner can be covered by two bolus injections of a fast acting, or a rapid acting or a very rapid acting insulin. As a result, a patient using intensive insulin therapy would only inject three, rather than four, times a day.

Experiments have been performed to demonstrate the importance of the addition of specific acids to hexameric insulin to enhance speed and amount of absorption and preserve bioactivity following dissociation into the monomeric form by addition of a chelator such as EDTA. Polyacids were selected based on their molecular size and structure to optimize association with hydrogen bonding sites on the insulin surface, effectively masking charged amino acid residues, FIG. 1, regardless of the source (including native insulin, recombinant insulin, long acting insulin, derivatives and analogues thereof). The acids were used at a concentration that provided optimal charge masking effect. As shown by the examples, the preferred acids are aspartic, glutamic and citric acid. These are added in addition to a chelator, preferably ethylenediaminetetraacetic acid (EDTA). The results show that the citric acid formulation, was more effective at dropping the blood glucose rapidly than the identical rapid acting formulation prepared with HCl in swine. Charge masking by the polyacid appears to be responsible for rapid insulin absorption. EDTA was not effective when used with adipic acid, oxalic acid or HCl at hastening the absorption of insulin. These studies establish the importance of the acid and chelator in both in vitro (human oral epithelial cells) and in vivo (rat and pig) assays and confirm the results seen in clinical subjects and patients with diabetes treated with the rapid acting insulin in combination with citric acid and EDTA.

DETAILED DESCRIPTION OF THE INVENTION

I. Compositions

A. Insulin

Figure 1:
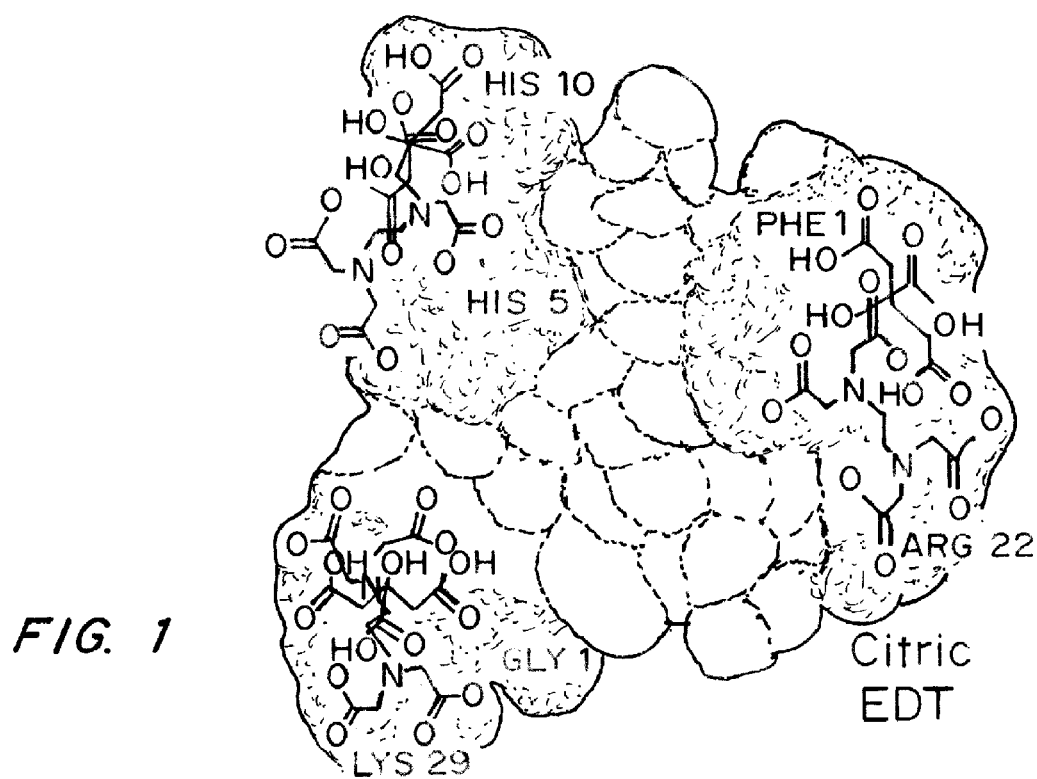
FIG. 1 is a three dimensional schematic of insulin showing charges.

As generally used herein, a drug is considered "highly soluble" when the highest dose strength is soluble in 250 ml or less of aqueous media over the pH range of 1-7.5. The volume estimate of 250 ml is derived from typical bioequivalence (BE) study protocols that prescribe administration of a drug product to lasting human volunteers with a glass (about 8 ounces) of water. A drug is considered highly soluble when 90% or more of an administered dose, based on a mass determination or in comparison to an intravenous reference dose, is dissolved. Solubility can be measured by the shake-flask or titration method or analysis by a validated stability-indicating assay.

As generally used herein, an immediate release drug formulation is considered "rapidly dissolving" when no less than 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

The composition includes a rapid or intermediate acting insulin (jointly referred to as "rapid acting" unless otherwise specified) and a long acting insulin. The rapid acting insulin is provided at a low pH, at which the long acting insulin does not precipitate when mixed together, even over a wide range of ratios of rapid acting to long acting insulin.

There are several differing types of commercial insulin available for diabetes patients. These types of insulins vary according to (1) how long they take to reach the bloodstream and start reducing blood glucose levels; (2) how long the insulin operates at maximum strength; and (3) how long the insulin continues to have an effect on blood sugar.

Rapid and Intermediate Acting Insulin.

Some diabetes patients use rapid-acting insulin at mealtimes, and also long-acting insulin for 'background' continuous insulin. This type of insulin starts working within 6 hours and provides a continuous level of insulin activity for up to 36 hours. Long-acting insulin operates at maximum strength after about 8-12 hours, sometimes longer.

At present there are three types of rapid-acting commercial insulin available; lispro insulin (Lysine-Proline insulin, sold by Eli Lilly as HUMALOG®), glulisine insulin (sold by Sanofi-Aventis as APIDRA®) and aspart insulin (sold by Novo Nordisk as NOVOLOG®). Biodel also has a proprietary insulin formulation that is in clinical trials, referred to as VIAJECT™. This is an insulin formulated with EDTA and citric acid, having a pH of 4.0.

Characterized by a cloudy appearance, intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains working for approximately 24 hours.

Types of intermediate-acting insulin include NPH (Neutral Protamine Hagedorn) and lente insulin. NPH insulin contains protamine which slows down the speed of absorption so that the insulin takes longer to reach the bloodstream but has a longer peak and lifespan. This means that fewer insulin injections are needed each day.

Long Acting Insulin

LANTUS® (glargine) is a recombinant human insulin analog that can have up to 24 hour duration. It differs from human insulin by having a glycine instead of asparagine at position 21 and two arginines added to the carboxy-terminus of the beta-chain. LANTUS® consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml). The pH is adjusted with HCl to 4.0.

The median time between injection and the end of the pharmacological effect for a maximum of 24 hours after the injection. The median time between injection and the end of pharmacological effect was 14.5 hours (range 9.5 to 19.3 hours) for NPH human insulin, and 24 hours (range 10.8 to greater than 24.0 hours) for insulin glargine.

The package insert says not to mix LANTUS® with any other types of insulin, unlike most rapid acting and intermediate acting insulins.

B. Acid Stabilizers and Chelators

Add Stabilizers

A rapid or intermediate release insulin is combined with the long acting insulin glargine at a pH at which the glargine is soluble, typically 4.0. The range of pH is approximately 3.0 to 4.2. The preferred range is 3.8 to 4.1.

As demonstrated by the examples, the acid is added in an effective amount to mask the charges on the insulin molecule which are exposed upon dissociation into the monomeric or dimeric form. Preferred acids include aspartic, glutamic, succinic, fumaric, maleic and citric acid. The concentration range is 0.1 to 3 mg/ml acid, for solutions containing 0.5 to 4 mg insulin/ml.

Experiments have been performed to demonstrate the importance of the addition of specific acids to hexameric insulin to preserve bioactivity following dissociation into the monomeric form by addition of a chelator such as EDTA. Diacids were selected based on their molecular size and used at an optimal concentration that provided a charge masking effect for the insulin molecule. Acids were used at an optimal concentration for providing a charge masking effect for the insulin molecule shown in FIG. 1. These studies establish the importance of the acid in both in vitro (human oral epithelial cells) and in viva (rat and pig) assays.

In the case of insulin glargine, there is no precipitate formed on mixing with VIAJECT™ which also has a pH of 4, matching that of the insulin glargine. Ultimately, this combination provides rapid acting insulin to shut down hepatic gluconeogenesis, carry the patient through a meal with less bolus insulin, thereby reducing the chance of hypoglycemia and provides 24 hr long lasting basal insulin, reducing the number of injections required/day from four to three.

Chelators

In the preferred embodiment, a metal chelator is mixed with the active agent. The chelator may be ionic or non-ionic. Suitable chelators include ethylenediaminetetraacetic acid (EDTA), citric acid, dimercaprol (BAL), penicillamine, alginic acid, chlorella, cilantro, alpha lipoic acid, dimercaptosuccinic acid (DMSA), dimercaptopropane sulfonate (DMPS), and oxalic acid. In the preferred embodiment, the chelator is EDTA. The chelator hydrogen bonds with the active agent, thereby masking the charge of the active agent and facilitating transmembrane transport of the active agent.

For example, when the active agent is insulin, in addition to charge masking, it is believed that the chelator pulls the zinc away from the insulin, thereby favoring the monomeric form of the insulin over the hexameric form and facilitating absorption of the insulin by the tissues surrounding the site of administration (e.g. mucosa, or fatty tissue).

Ions may be part of the active agent, added to the stabilizing agent, mixed with the chelator, and/or included in the coating. Representative ions include zinc, calcium, iron, manganese, magnesium, aluminum, cobalt, copper, or any di-valent metal or transitional metal ion. $Zn^{+2}$ has a stronger binding preference for EDTA than $Ca^{+2}$.

The formulation also includes a metal chelator. The chelator may be ionic or non-ionic. Suitable chelators include ethylenediaminetetraacetic acid (EDTA), citric acid, dimercaprol (BAL), penicillamine, alginic acid, chlorella, cilantro, alpha lipoic acid, dimercaptosuccinic acid (DMSA), dimercaptopropane sulfonate (DMPS), and oxalic acid. In the preferred embodiment, the chelator is EDTA. In addition to charge masking, it is believed that the chelator pulls the zinc away from the insulin, thereby favoring the monomeric form of the insulin over the hexameric form and facilitating absorption of the insulin by the tissues surrounding the site of administration (e.g., mucosa, or fatty tissue). Optionally, the chelator and solubilizing agent are the same compound. Ions may be part of the active agent, added to the stabilizing agent, mixed with the chelator, and/or included in the coating. Representative ions include zinc, calcium, iron, manganese, magnesium, aluminum, cobalt, copper, or any di-valent metal or transitional metal ion. $Zn^{+2}$ has a stronger binding preference for EDTA than $Ca^{+2}$.

C. Formulations

The active compounds (or pharmaceutically acceptable salts thereof) may be administered in the form of a pharmaceutical composition wherein the active compound(s) is in admixture or mixture with one or more pharmaceutically acceptable carriers, excipients or diluents. In a preferred embodiment the insulin is administered by injection. Alternatively, the compositions may be administered by buccal administration, sublingual administration, vaginal administration, rectal administration, or nasal administration.

Diluents

The formulation for injection will typically be suspended in sterile water, phosphate buffered saline, or saline. Other suitable pharmaceutically acceptable agents are known. These will typically be added to the insulin in lyophilized or dried form immediately before use, but may be added prior to use.

Solubilizing Agents

Solubilizing agents include wetting agents such as polysorbates and poloxamers, non-ionic and ionic surfactants, food acids and bases (e.g. sodium bicarbonate), and alcohols, and buffering acids or salts for pH control. pH is typically adjusted with food acids and bases (e.g. sodium bicarbonate), and alcohols, and buffer salts for pH control.

Gels or Films

Gels or films are formed by mixing one or more by hydrophilic polymers in solution, which gel or solidify by ionic and/or covalent binding. Suitable materials include, but are not limited to, starch, pregelatinized starch, gelatin, sugars (including sucrose, glucose, dextrose, lactose and sorbitol), dextrin, maltodextrin, polyethylene glycol, waxes, natural and synthetic gums such as acacia, guar gum, tragacanth, alginate, sodium alginate, celluloses, including hydroxypropylmethylcellulose, carboxymethylcellulose sodium, hydroxypropylcellulose, hydroxylethylcellulose, ethylcellulose, methyl cellulose, and veegum, hydrogenated vegetable oil, Type I, magnesium aluminum silicate, and synthetic polymers such as acrylic acid and methacrylic acid copolymers, carbomer, methacrylic acid copolymers, methyl methacrylate copolymers, aminoalkyl methacrylate copolymers, polyacrylic acid/polymethacrylic acid, and polyvinylpyrrolidone. Blending or copolymerization sufficient to provide a certain amount of hydrophilic character can be useful to improve wettability and mucoadhesion of the materials. For example, about 5% to about 20% of monomers may be hydrophilic monomers. Hydrophilic polymers such as hydroxylpropylcellulose (HPC), hydroxpropylmethylcellulose (HPMC), carboxymethylcellulose (CMC) are commonly used for this purpose. Preferably, the polymers are bioerodable, with preferred molecular weights ranging from 1000 to 15,000 Da, and most preferably 2000 to 5000 Da. These can also be nonionic polymers such as ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

In one embodiment, the formulation is a sublingual solid formulation that contains excipients, such as poly(vinyl alcohol), glycerin, carboxymethyl cellulose (CMC), and optionally poly(ethylene glycol) and water. The composition may be in the form of a clear or opaque, flexible, thin material. Typical thicknesses range from 0.01 to 2 mm. The film may have any suitable shape, including round, oval, rectangle, or square. The film may be a monolayer, bilayer or trilayer film. In the preferred embodiment, the film is designed to be suitable for sublingual administration. The monolayer film contains an active agent and one or more excipients. The bilayer film contains one or more excipients, such as a solubilizing agent and/of a metal chelator, in a first layer, and an active agent in the second layer. This configuration allows the active agent to be stored separated from the excipients, and may increase the stability of the active agent, and optionally increases the shelf life of the composition compared to if the excipients and active agent were contained in a single layer. The trilayer film contains three layers of film. Each of the layers may be different, or two of the layers, such as the bottom and top layers, may have substantially the same composition. In one embodiment the bottom and top layers surround a core layer containing the active agent. The bottom and top layers may contain one or more excipients, such as a solubilizing agent and a metal chelator. Preferably the bottom and top layers have the same composition. Alternatively, the bottom and top layers may contain different excipient(s), or different amounts of the same excipient(s). The core layer typically contains the insulin, optionally with one or more excipients. In one embodiment, the film is a bilayer film that contains EDTA and citric acid in one layer and insulin in the second layer. Each layer may contain additional excipients, such as glycerin, polyvinyl alcohol, carboxymethyl cellulose, and optionally PEG (such as PEG 400 or PEG 1600). In one embodiment, a third layer can be located between the insulin layer and the layer containing the other ingredients to further protect the active agent from degradative ingredients located in the other layer during storage. Suitable materials for the protective layer include carboxymethylcellulose sodium, carnauba wax, cellulose acetate phthalate, cetyl alcohol, confectioner's sugar, ethylcellulose, gelatin, hydroxyethyl cellulose, hydroxypropyl methylcellulose, liquid glucose, maltodextrin, methylcellulose, microcrystalline wax, polymethacrylates, polyvinyl alcohol, shellac, sucrose, talc, titanium dioxide, and zein. By altering the composition of the excipients, the film can be designed to dissolve rapidly (less than 30 seconds) or slowly (up to 15 minutes) in order to achieve the desired absorption profile and subsequent effect. The film may dissolve in a time period ranging from 3 to 5 minutes, 5 to 8 minutes, or 8 to 12 minutes. Preferably, the film dissolves in a time period ranging from 15 seconds to 2 minutes.

There are a number of colorings and flavorings that are commercially available. Flavorings include mint, lemon, bubblegum, and other standard flavors. Sweeteners can be added, including non-glucose sweeteners, which are particularly advantageous for administration of insulin. Colorings can be red, blue, green, yellow, orange, or any other standard FDC approved color.

Stabilizers are used to inhibitor retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethaholamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins; and synthetic detergents, such as diosctanoylphosphatidyl choline and polyethylenepolypropylene glycol). Other suitable stabilizers include acacia, albumin, alginic acid, bentonite, carboxymethylcellulose calcium, carboxymethylcellulose sodium, cyclodextrins, glyceryl monostearate, hydroxypropyl cellulose, hydroxypropyl methylcellulose, magnesium aluminum silicate, propylene glycol, propylene glycol alginate, sodium alginate, white wax, xanthan gum, and yellow wax. In the preferred embodiment, the agent is insulin and the stabilizer may be a combination of one or more polysaccharides and glycerol, bacteriostatic agents, isotonic agents, lecithins, or synthetic detergents.

II. Methods of Making the Formulations

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Proper formulation independent upon the route of administration chosen.

III. Methods of Using Formulations

The formulations may be administered in a variety of manners, including by infection, preferably subcutaneously, or topically to a mucosal surface such as buccal administration, nasal administration, sublingual administration, rectal administration, vaginal administration, pulmonary, or ocular administration. Subcutaneous, buccal or sublingual are preferred. Following administration, the dosage form dissolves quickly releasing the drug or forming small particles containing drug, optionally containing one or more excipients. The formulation is designed to be rapidly absorbed and transported to the plasma for systemic delivery.

Formulations containing insulin as the active agent may be administered to a type 1 or type 2 diabetic patient before or during a meal. Due to the rapid absorption, the compositions can shut off the conversion of glycogen to glucose in the liver, thereby preventing hyperglycemia, the main cause of complications from diabetes. Loss of the body's ability to shut off conversion of glycogen to glucose by the liver during digestion of a meal is one of the first symptom of type 2 diabetes.

In the preferred embodiment, the formulation is formed by mixing a powdered active agent with a liquid diluent that contains a pharmaceutically acceptable liquid carrier and one or more solubilizing agents. In the most preferred embodiment, the active agent is insulin, and the diluent contains saline or glycerin, EDTA and citric acid. Prior to administration the powder and diluent are mixed together to form an injectable composition.

Insulin usually is given by subcutaneous (beneath the skin) injection. Insulin is generally included in a dosage range of 3-50 IU per human dose. For insulin with only 2.5% bioavailability, an oral dose of 2,000 IU will deliver a 50 IU systemically available dose. For insulin with a much greater bioavailability, such as a 50% bioavailability, the delivery of a 3 IU systemically available dose is achieved by administration of a 6 IU dose. The amount of insulin needed varies greatly among patients, and depends an diet, other diseases, exercise, and other drugs and may change with time. A doctor can determine how often and at what time of day to inject the insulin, as well as what type of insulin will best control the level of sugar in the blood.

The different types of insulin vary as to how quickly they are absorbed and reach maximal levels in the blood and how long sufficient levels to reduce blood sugar are maintained. For example, for formulations not containing the acids and chelator described above, last-acting insulins such as insulin Lispro reach maximal concentrations in the blood in 30-60 minutes and remain effective for 5-8 hours; long-acting insulins, such as Ultralente, start to work in 2-4 hours and continue working for 24 hours. The combination formulation can be adjusted to provide for continuous results over an extended period of time, with resulting schedules requiring injections once, twice or three times a day.

The formulation is designed to be rapidly absorbed and transported to the plasma for systemic delivery. Formulations may be administered to a type 1 or type 2 diabetic patient before or during a meal. The formulation is typically administered by subcutaneous injection. The formulation may also be administered by buccal, nasal or pulmonary administration. Due to the rapid absorption, the compositions can shut off the conversion of glycogen to glucose in the liver, thereby preventing hyperglycemia, the main cause of complications from diabetes and the first symptom of type 2 diabetes. Loss of the body's ability to shut off conversion of glycogen to glucose by the liver during digestion of a meal is one of the first symptoms of type 2 diabetes.

The present invention will be further understood by reference to the following non-limiting examples.

Example 1

Effect of EDTA on Insulin Absorption Through an Epithelial Cell Multilayer Device Purpose: To demonstrate in vitro the effect of EDTA in the presence of citric acid on absorption of insulin through an epithelial cell multilayer.

Materials and Methods

Figure 2:
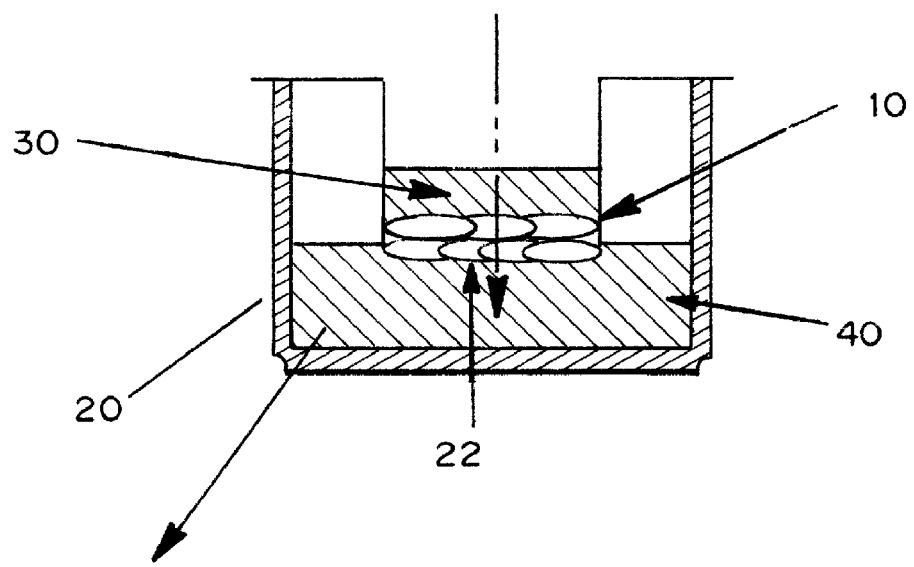
FIG. 2 is a diagram of the transwell device used to measure insulin absorption through oral epithelial cells.

Two saline solutions were mixed. The first contained 1 mg/ml insulin, 2 mg/ml EDTA and 2 mg/ml citric acid ("solution 1"). The second contained 1 mg/ml insulin and 2 mg/ml citric acid ("solution 2"). The control (no cells) contained EDTA, citric acid and insulin. Immortalized human epithelial cell line cultures (10) were seeded on transwell plates (20) FIG. 2. Cells were grown to confluence and tested for membrane integrity using trans-epithelial resistance. A 0.1 μm filter (22) was used. At time zero, the fluid in the top chambers, i.e., donor chamber (30), of the transwell plates was replaced with 0.5 ml of insulin solution, either solution 1 or solution 2. Two plates with solution 1, two plates with solution 2 and one plate with the control solution (no cells) were tested simultaneously. The lower chamber, i.e., receiver chamber (40) of each plate contained 1.5 mL of saline solution. At each time point, 100 μL of fluid from the lower chamber (40) was removed and analyzed with insulin Enzyme-Linked Immunosorbent Assay (ELISA). 100 μL of saline was added to the lower chamber to maintain a constant volume of 1.5 mL throughout the study.

The amount of insulin removed from the lower chamber at each time point was added to the amount removed in the previous time point(s) to determine the cumulative amount of insulin recovered in the lower chamber. Cells were stained to check for viability before and after the experiment. There was no statistical difference in the cell viability for each of the plates.

Results

Figure 3:
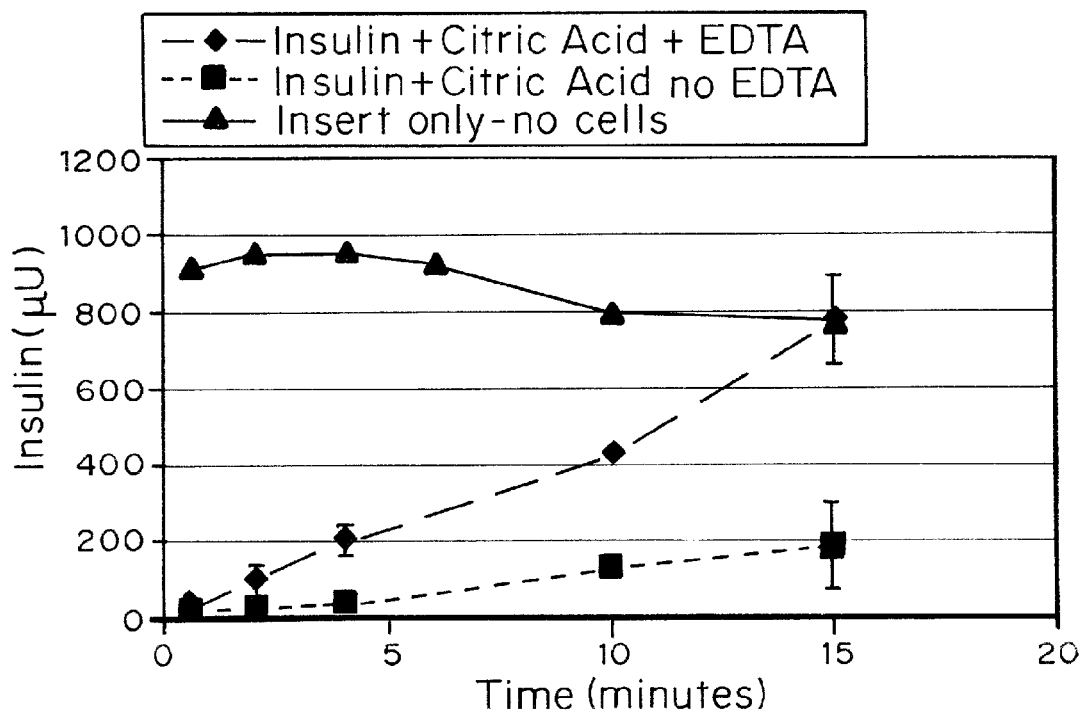
FIG. 3 is a graph of the mean insulin accumulation (μU) over time (minutes) in the lower chamber of a transwell membrane plate seeded with epithelial cells, comparing the effect of an insulin formulation containing EDTA (♦) with one without EDTA (■), with a control, no cells (▲).

FIG. 3 is a graph of the mean insulin accumulation (μU) over time (minutes) in the lower chamber of a transwell plate seeded with epithelial cells, comparing the effect of an insulin formulation containing EDTA (♦) with one without EDTA (■), with a control, no cells (▲).

Solution 1, which contained EDTA, moved through the multilayer of epithelial cells more effectively than solution 2, which did not contain EDTA. Therefore, the effect of combining EDTA with citric acid is to promote the speed and amount of absorption.

Example 2

Effect of Aspartic and Citric Acid on Absorption of Insulin Through an Epithelial Cell Multilayer Purpose: Demonstrate that polyacids have different affinities for insulin with EDTA as shown by an increase in absorption through cells.

Methods and Materials:

Oral epithelial cells that have been seeded on transwell plates were used to determine the rate of absorption through the cell multilayer, as described in example 1. Insulin (1 mg/ml) was dissolved in either aspartic (0.2 mg/mL) or citric acid (2 mg/ml) and EDTA (2 mg/ml) was added to both. Insulin with citric acid (no EDTA) was used as a control. The pH of the solution was approximately 3.5 to 4, and physiological saline was present to provide an isotonic environment for the cells (0.85% NaCl, sufficient to produce a range of 280-310 mOsm as measured by freezing point depression, Microsmette, Precision systems, Natick, Mass.). Samples were taken from the receiver chamber and assayed by ELISA (Linco Corp.) for human recombinant insulin (μU/mL).

Results

Figure 4:
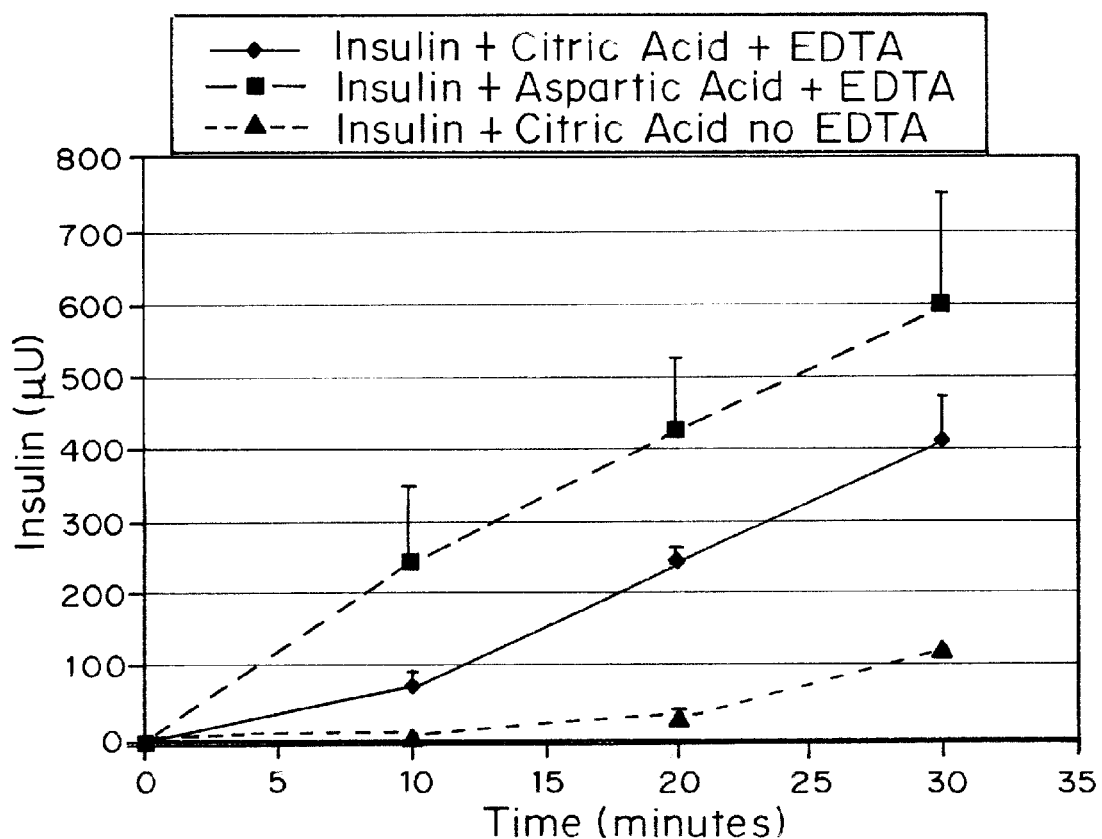
FIG. 4 is a graph of cumulative insulin (U) over time in minutes for samples of citric acid 1.8 mg/mg or aspartic acid, EDTA 1.8 mg/ml, insulin 0.9 mg/ml NaCl 0.85%, and a preservative m-cresol transferred through one set of epithelial cell layers.

Insulin/citric acid absorption through the cell layers was enhanced by the addition of EDTA (as seen in example 2). However, aspartic acid was even more potent at enhancing insulin transport in the presence of EDTA FIG. 4.

Conclusion: Different polyacids in the presence of EDTA have varying effects on insulin absorption, possibly due to varying degrees of charge masking.

Example 3

Effect of Acid on Absorption of Insulin from Polymeric Gel Administered Rectally to Rats Purpose: To observe effect of acids and EDTA in an in vivo model Material and Methods Samples Insulin was incorporated into a gel consisting of PVA (0.5%), Carbopol (2.7%), CMC (0.005%) and PEG 400 (0.14%), glycerin (0.14%), and EDTA (0.005%) by blending with insulin/aspartic acid or insulin/HCl. The final concentration of insulin in insulin/aspartic acid gel was 0.7 and insulin concentration in insulin/HCl gel was 1.7 mg/g.

Rat Rectal Study:

Rats were fasted overnight and were cleared of all fecal matter with a warm water enema. Then the gel formulation was inserted into the rectum and the rat's blood glucose was monitored over an 8 hour time period.

Results

Figure 5:
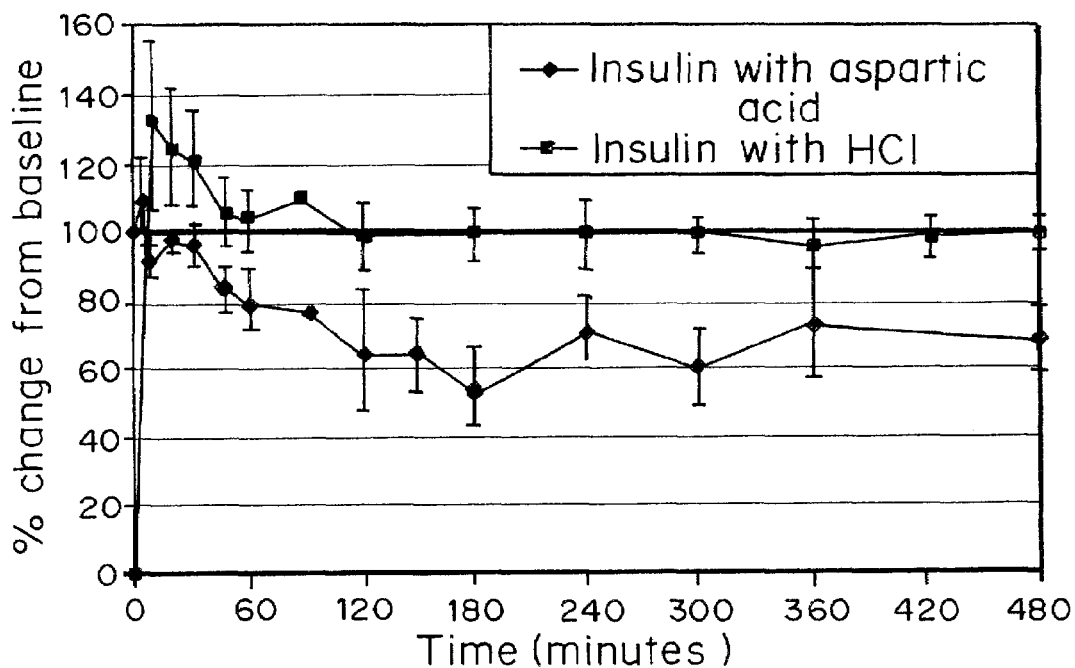
FIG. 5 is a graph of percent glucose lowering from baseline over time in minutes comparing insulin with aspartic acid and EDTA with insulin with HCl and EDTA.

The results are shown in FIG. 5 as a percent glucose lowering from baseline comparing insulin with aspartic acid and EDTA to insulin with HCl and EDTA. The results show significantly better lowering of glucose for the insulin containing aspartic acid as compared to insulin containing HCl.

Example 4

Comparison of Effect of Citric Acid, Glutamic Acid, Adipic Acid and Oxalic Acid on Insulin Absorption Through an Epithelial Cell Multilayer Materials and Methods Transwell plates seeded with oral epithelial cells were used for these experiments. The effect of EDTA was monitored by the amount of insulin that came through the lower chamber of the transwell plate.

Oral epithelial cells were grown on transwell inserts for 2 weeks until multiple (4-5) cell layers had formed. Transport studies were conducted by adding the appropriate solution (all contained 1 mg/ml human insulin) to the donor well and removing samples from the receiver well after 10 minutes. Insulin amounts in the receiver wells were assayed using ELISA. Apparent Permeability was calculated using the formula: Apparent Permeability=Q/A(C)t where Q=total amount permeated during incubation time in μg, A=area of insert in cm². C=initial concentration in donor well in μg/cm³ and t=total time of experiment in sec.

EDTA concentration is 0.45 mg/mL in all cases and the acid concentrations are as follows: Citric add 0.57 mg/ml, Glutamic acid 0.74 mg/mL. Adipic acid 0.47 mg/mL, Oxalic acid 0.32 mg/mL. The pH of the solutions was 3.6 in all cases.

Results

Figure 6:
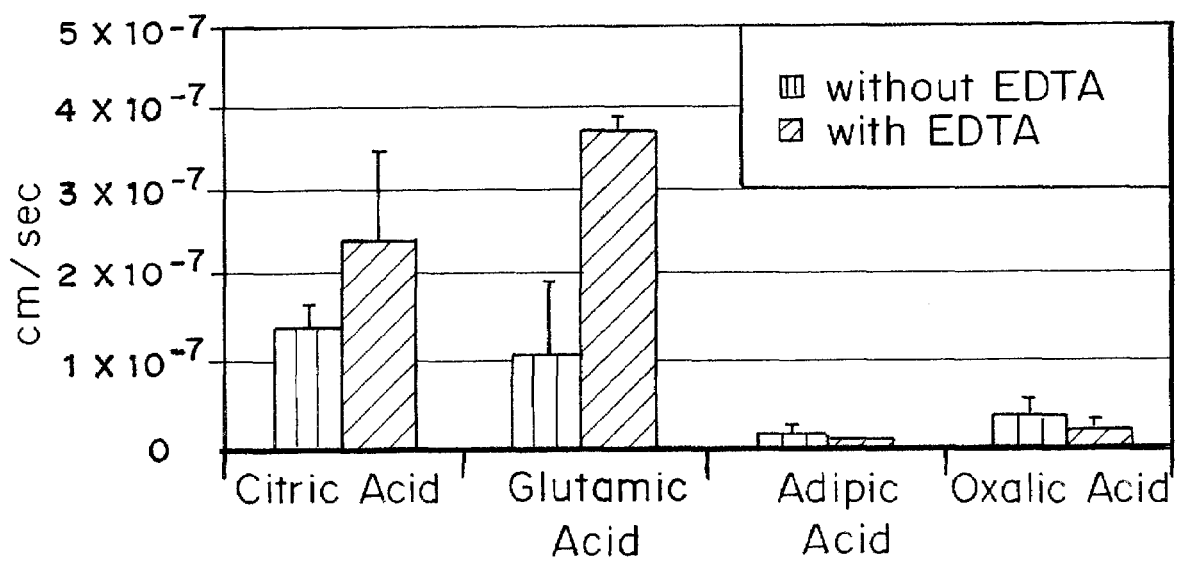
FIG. 6 is a graph of insulin apparent permeability for insulin with (solid) and without (hatched) EDTA, for samples with citric acid, glutamic, adipic, and oxalic acid, over time in minutes.

FIG. 6 shows the results with samples of organic polyacids that have been tested, with and without EDTA. The results show that there is an increase in the cumulative amount of insulin apparent permeability when EDTA is added to the acid/insulin in the case of citric and glutamic acids. This did not hold true for all organic polyacids. Adipic and oxalic acids did not show such a response.

Example 5

Comparison of Effect of HCl and Citric Acid on Absorption of Insulin with EDTA in Miniature Diabetic Swine Purpose: To look at timing of glucose response when insulin is injected with a polyacid or organic acid in conjunction with EDTA.

Materials and Methods

To further demonstrate that the type of acid is important to the rapid action of the dissociated insulin, a comparison of citric acid to HCl, was performed in miniature diabetic swine. Insulin (0.9 mg/mL) was prepared as a clear isotonic solution containing citric acid (1.8 mg/mL), EDTA (1.8 mg/mL), and m-cresol as a preservative, pH ~4. The comparator was prepared in the same manner, substituting HCl (0.001N) for citric acid and adjusting the pH with NaOH to approximately 4.

Diabetic mini pigs were not fed on the day of the study and were dosed with 0.08 U/kg, on three occasions with the HCl formulation. For comparison, the citric acid formulation was used on two occasions with this dose, and four other occasions at a higher dose of 0.125 U/kg. Blood was drawn for insulin and glucose determination over the 8 hour study period.

Figure 7:
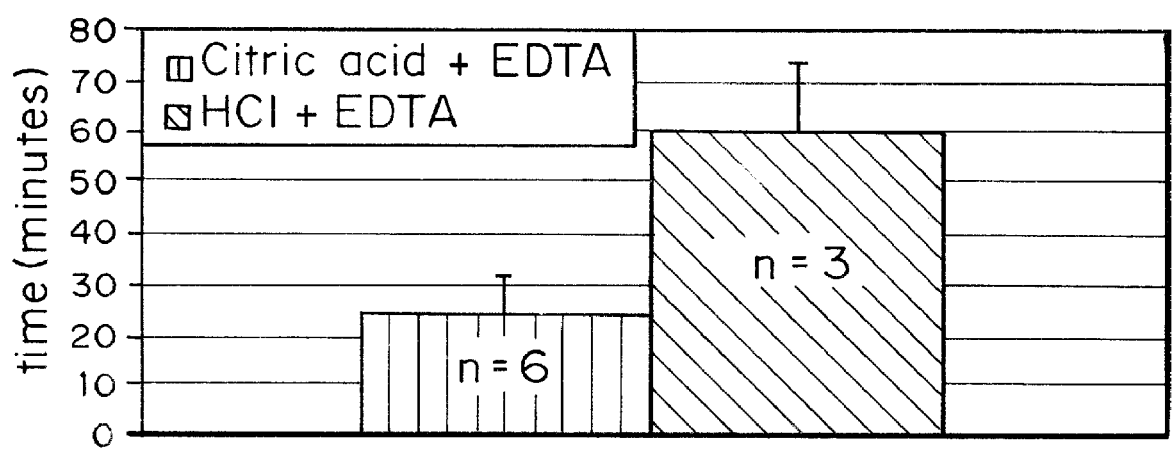
FIG. 7 is a graph of mean glucose levels in miniature swine over time, comparing insulin with EDTA and citric acid versus insulin with EDTA and HCl.

Results:

The results compare the time to reach the lowest glucose level (nadir) following insulin administration to diabetic mini-pigs FIG. 7. Citric acid was consistently faster at reaching the nadir than an identical formulation made with HCl.

Modifications and variations of the formulations and methods of use will be obvious to those skilled in the art from the foregoing detailed description and are intended to come within the scope of the appended claims.

We claim:

1. A composition comprising a rapid or intermediate acting insulin in combination with a long acting insulin, wherein the pH of the composition is adjusted to a pH of between 3.8 and 4.2 to solubilize the long acting insulin.

2. The composition of claim 1, comprising glargine insulin.

3. The composition of claim 1, comprising a rapid acting insulin in combination with a long acting insulin, further comprising an intermediate acting insulin.

4. The composition of claim 1, comprising a chelator selected from the group consisting of ethylenediaminetetraacetic acid (EDTA), dimercaprol (BAL), penicillamine, alginic acid, Chlorella, Cilantro, Alpha Lipoic Acid, Dimercaptosuccinic Acid (DMSA), dimercaptopropane sulfonate (DMPS), and oxalic acid.

5. The composition of claim 4, wherein the chelator is ethylenediaminetetraacetic acid (EDTA).

6. The composition of claim 1, comprising an acid selected from the group consisting of aspartic acid, glutamic acid, and citric acid.

7. The composition of claim 1 comprising a chelator, and an acid selected from the group consisting of aspartic acid, glutamic acid and citric acid.

8. The formulation of claim 7 comprising EDTA.

9. The formulation of claim 7 comprising citric acid.

10. The formulation of claim 7 comprising a rapid acting insulin wherein the ratio of insulin:EDTA:citric acid is 1:2:2.

11. The formulation of claim 7 wherein the insulin is selected from the group consisting of native human insulin, recombinant human insulin, a derivative of human insulin, and an analog of human insulin suitable for administration to a human.

12. A method of treating a patient with insulin comprising administering to an individual the composition of any of claims 1 or 7.

13. The method of claim 12 wherein the insulin is administered by injection.

14. The method of claim 12 wherein the insulin is in a formulation for administration sublingually.

* * * * *